United States Patent [19]
Ohmizu et al.

[11] Patent Number: 5,629,419
[45] Date of Patent: May 13, 1997

[54] PROCESS FOR PREPARING 4-MERCAPTOPYRROLIDINE INTERMEDIATE COMPOUNDS AND A PROCESS FOR THEIR USE IN PREPARING CARBAPENEM -2-EM-3 CARBOXYLIC ACIDS

[75] Inventors: Hiroshi Ohmizu, Kyoto; Masahiko Seki, Nagaokakyo; Takeshi Yamanaka, Osaka, all of Japan

[73] Assignee: Tanabe Seiyaku Co., Ltd., Osaka, Japan

[21] Appl. No.: 555,204

[22] Filed: Nov. 8, 1995

[30] Foreign Application Priority Data

Nov. 24, 1994 [JP] Japan .................................. 6-288517

[51] Int. Cl.$^6$ .................. C07D 207/24; C07D 487/04
[52] U.S. Cl. ................................ 540/350; 548/544
[58] Field of Search .......................... 540/350; 548/544

[56] References Cited

U.S. PATENT DOCUMENTS 4,173,569  11/1979  Banfi et al. .

FOREIGN PATENT DOCUMENTS

| | | |
|---|---|---|
| 0223328 | 5/1987 | European Pat. Off. . |
| 0337637 | 10/1989 | European Pat. Off. . |
| 0338435 | 10/1989 | European Pat. Off. . |
| 0474243 | 3/1992 | European Pat. Off. . |
| 0604857 | 7/1994 | European Pat. Off. . |
| 2380257 | 9/1978 | France . |
| 5279328 | 10/1993 | Japan . |
| 599151 | 5/1978 | Switzerland . |

OTHER PUBLICATIONS

Chemical Abstracts, vol. 82, No. 3, 20 Jan. 1975. Abstract No. 16463g.
Chemical Abstracts, vol. 98, No. 9, 28 Feb. 1983. Abstract No. 71602g.
Chemical Abstracts, vol. 98, No. 9, 28 Feb. 1983. Abstract No. 71842k.
Synthetic Methods of Organic Chemistry, vol. 14, pp. 234, 1960. No. 493.
Synthetic Methods of Organic Chemistry, vol. 19, pp. 400, 1965. No. 952.
"Ulmann's Encyclopedia of Industrial Chemistry", 5th edition, vol. A5, p. 247, point 12.3, 1986.

*Primary Examiner*—David B. Springer
*Attorney, Agent, or Firm*—Browdy and Neimark

[57] ABSTRACT

An improved process for preparing a 4-mercaptopyrrolidine compound [I]:

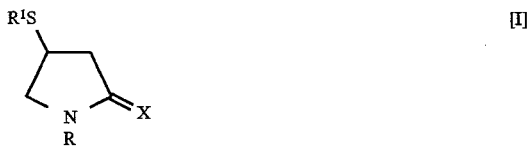

wherein R is H, lower alkyl or lower alkanoyl, $R^1$ is H or SH-protecting group, and X is O or S, which comprises reacting halogenobutyric acid compound [VI], or a salt thereof, with amine compound [VII], or a salt thereof, and if necessary, followed by thiocarbonylating the product and/or removing the protecting group, said 4-mercaptopyrrolidine compound [I] being useful as intermediate for carbapenem antibacterial agents.

8 Claims, No Drawings

PROCESS FOR PREPARING 4-MERCAPTOPYRROLIDINE INTERMEDIATE COMPOUNDS AND A PROCESS FOR THEIR USE IN PREPARING CARBAPENEM -2-EM-3 CARBOXYLIC ACIDS

TECHNICAL FIELD

The present invention relates to a process for preparing 4-mercaptopyrrolidine compounds.

PRIOR ART

4-Mercaptopyrrolidine compounds having an oxo group or a thioxo group at the 2-position of the pyrrolidine nucleus are very useful compounds for use as an intermediate for preparing various drugs, for example, carbapenem antibacterial agents. For example, a 2-oxo compound thereof, i.e. (4-mercaptopyrrolidin-2-one) has been used as an intermediate for preparing 2-(pyrrolidin-2-on-4-ylthio)-6-(1-hydroxyethyl)-1-methylcarbapen-2-em-3-carboxylic acid (cf. European Patent Publication No. 337637). The corresponding 2-thioxo compound thereof has also been used as an intermediate for preparing carbapenem antibacterial agents (cf. European Patent Publication No. 474243).

In the conventional method, 4-mercaptopyrrolidine compounds have been prepared from a mono-methyl ester of aspartic acid through 3-benzylthio-3-cyanopropionic acid methyl ester (cf. Japanese Patent First Publication (Kokai) No. 279328/1993). However, the yield of 4-mercaptopyrrolidine compound in the conventional method is not sufficient, for example, merely several % yield calculated from commercially available aspartic acid.

BRIEF DESCRIPTION OF THE INVENTION

An object of the present invention is to provide an improved process for preparing a 4-mercaptopyrrolidine compound being useful as an intermediate in higher yield at a lower cost, than conventional processes.

Another object of the present invention is to provide a novel halogenobutyric acid compound which is used in the preparation of a 4-mercaptopyrrolidine compound as a starting compound, particularly a 3-phenyl-lower alkylthio-4-halogenobutyric acid lower alkyl ester. It has never been known to prepare a 4-mercaptopyrrolidine compound through said compound.

DETAILED DESCRIPTION OF THE INVENTION

According to the present invention, a 4-mercaptopyrrolidine compound of the formula [I]:

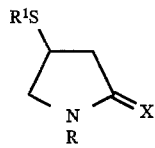

wherein R is a hydrogen atom, a lower alkyl group or a lower alkanoyl group, $R^1$ is a hydrogen atom or a protecting group for thiol group, and X is an oxygen atom or a sulfur atom, is prepared by (i) reacting a halogenosuccinic acid compound of the formula [II]:

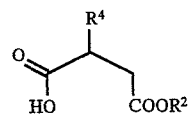

wherein $R^2$ is a hydrogen atom or a protecting group for carboxyl group, and $R^4$ is a halogen atom, or a salt thereof, with a thiol compound of the formula [III]:

$R^{11}SH$ [III]

wherein $R^{11}$ is a protecting group for thiol group, or a salt thereof, to give a nercaptosuccinic acid compound of the formula [IV]:

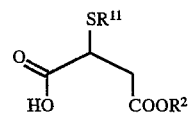

wherein $R^{11}$ and $R^2$ are the same as defined above, or a salt thereof, (ii) subjecting the compound [IV] or a salt thereof to reduction to give a hydroxybutyric acid compound of the formula [V]:

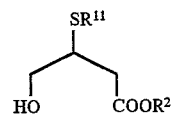

wherein $R^{11}$ and $R^2$ are the same as defined above, or a salt thereof, (iii) halogenating the compound [V] or a salt thereof to give a halogenobutyric compound of the formula [VI]:

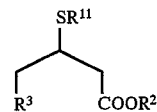

wherein $R^3$ is a halogen atom, and $R^{11}$ and $R^2$ are the same as defined above, or a salt thereof, (iv) reacting the compound [VI] or a salt thereof with an amine compound of the formula [VII]:

$RNH_2$ [VII]

wherein R is the same as defined above, or a salt thereof, and if necessary, (v) followed by thiocarbonylating the product and/or removing the protecting group for thiol group from the product.

The protecting group for carboxyl group may be any group which does not affect the reaction of the compound [II] and the compound [III], the reduction of the compound [IV] and the halogenation of the compound [V], but is easily removed during the reaction of the compound [VI] and the amine compound [VII], for example, a lower alkyl group, a phenyl-lower alkyl group, etc., but a lower alkyl group is more preferable.

The protecting group for thiol group may be any group which does not affect the reaction of the compound [II] and the compound [III], the reduction of the compound [IV], the halogenation of the compound [V] and the reaction of the compound [VI] and the amine compound [VII], but is easily removed by treatment with a base or an acid, reduction using a metal, or cathodic reduction, for example, a substituted or unsubstituted phenyl-lower alkyl group, a lower alkanoyl group, etc., but a phenyl lower alkyl group is more preferable.

The halogen atom for $R^3$ and $R^4$ is chlorine atom, bromine atom, etc., but the halogen atom for $R^3$ is preferably chlorine atom, and the halogen atom for $R^4$ is preferably bromine atom.

The salt of the compound [II], the compound [IV], the compound [V] and the compound [VI] is preferably an alkali metal salt and an alkaline earth metal salt. The salt of the compound [III] is preferably an alkali metal salt, and the salt of the amine compound [VII] is preferably a salt with an inorganic acid.

The reaction of the halogenosuccinic acid compound [II] or a salt thereof and the thiol compound [III] or a salt thereof is carried out in an appropriate solvent. The solvent may be any one which does not affect the reaction, and may be preferably ethanol, water, etc., but ethanol is especially preferable. The reaction is preferably carried out under cooling or at room temperature, for example, at a temperature from −78° C. to 30° C.

The reduction of the mercaptosuccinic acid compound [IV] or a salt thereof is carried out in the presence of a reducing agent in an appropriate solvent. The solvent may be any one which does not affect the reduction reaction, for example, tetrahydrofuran, etc. The reducing agent includes conventional ones such as an alkali metal borohydride, boran, etc., but diboran-di-lower alkyl sulfide is more preferable. The reaction is preferably carried out under cooling or at room temperature, for example, at a temperature from −78° C. to 30° C.

The halogenation of the hydroxybutyric acid compound [V] or a salt thereof is carried out in the presence of a halogenating agent and a base in an appropriate solvent. The solvent may be any one which does not affect the halogenation, for example, chloroform, etc. The halogenating agent includes any conventional ones, for example, thionyl chloride, sulfuryl chloride, tributylphosphine-carbon tetrachloride, triphenylphosphine-carbon tetrachloride, etc. The base includes an organic base such as pyridine, and an inorganic base such as an alkali metal hydroxide, an alkali metal hydrogen carbonate, an alkali metal carbonate, etc. The reaction is preferably carried out under cooling or with heating, for example, at a temperature from −78° C. to 50° C.

The reaction of the halogenobutyric acid compound [VI] and the amine compound [VII] is carried out in an appropriate solvent. The solvent is preferably methanol, ethanol, dimethylformamide, tetrahydrofuran, etc. The reaction is preferably carried out at room temperature or with heating, for example, at a temperature from 10° C. to 100° C.

By the above reactions, there is obtained a compound of the formula:

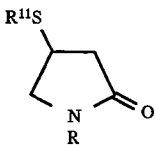

wherein $R^{11}$ and R are the same as defined above.

The thiocarbonylation of the above compound and the removal of the protecting group for thiol group from the above compound are carried out by a conventional method.

For example, the thiocarbonylation of the above compound is carried out by treating with a thioketonizing agent in an appropriate solvent. The thioketonizing agent includes, for example, 2,4-bis(4-methoxyphenyl)-1,3-dithia-2,4-diphosphetane-2,4-disulfide, 2,4-dimethyl-1,3-dithia-2,4-diphosphetane-2,4-disulfide, phosphorus pentasulfide, etc. The solvent may be any inert solvent, for example, dimethoxyethane, pyridine, xylene, toluene, benzene, etc. The reaction is preferably carried out at room temperature or with heating, for example, at a temperature from 10° C. to 200° C.

The removal of the protecting group for thiol group is carried out by using sodium in liquid ammonia when the protecting group is a phenyl-lower alkyl group. When the protecting group for thiol group is a substituted phenyl-lower alkyl group, it is removed in the presence of an acid in an appropriate solvent. The acid is preferably trifluoroacetic acid, and the solvent is preferably anisole. The reaction is preferably carried out at room temperature or with heating, for example, at a temperature from 10° C. to 100° C. When the protecting group for thiol group is a lower alkanoyl group, it is removed in the presence of a base in an appropriate solvent. The base is preferably ammonia, sodium methoxide, etc., and the solvent is preferably methanol. The reaction is preferably carried out under cooling, for example, at a temperature from −78° C. to 10° C.

The desired compound [I] thus obtained of the present invention can be converted into a 1-methylcarbapenem derivative of the formula [VIII]:

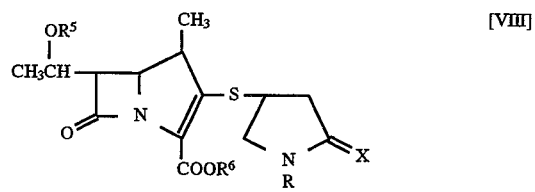

wherein $R^5$ is a hydrogen atom or a protecting group for hydroxy group, $R^6$ is a hydrogen atom or an ester residue, and X and R are the same as defined above, or a salt thereof, which is useful as an antibacterial agent, by a conventional method, for example, by the method disclosed in European Patent Publication No. 337637 or European Patent Publication No. 474243. For example, the compound [VIII] is prepared by reacting the compound [I] with a reactive derivative at the 2-oxo group of a ketone compound of the formula [IX]:

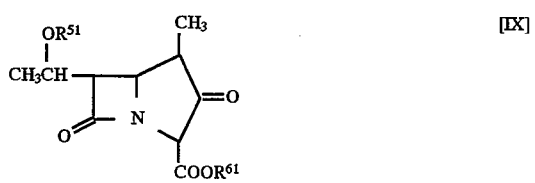

wherein $R^{51}$ is a hydrogen atom or a protecting group for hydroxy group, and $R^{61}$ is a hydrogen atom or an ester residue, and when $R^{51}$ is a protecting group for hydroxy group and/or $R^{61}$ is an ester residue which may be a protecting group for carboxyl group, followed by removing said protecting group and/or said ester residue from the product, and if necessary, by converting the product into a pharmaceutically acceptable ester or salt thereof.

The reactive derivative at the 2-oxo group of the ketone compound [IX] may be any conventional derivative, for example, a compound of the formula [IX-a]:

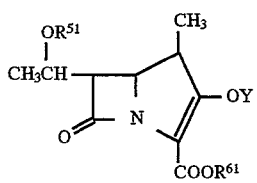

wherein Y is a diphenylphosphoryl group, a di-lower alkyl-substituted phenylphosphoryl group, a di-lower alkylphosphoryl group, a lower alkanesulfonyl group, a phenylsulfonyl group or a lower alkyl-substituted phenylsulfonyl group, and $R^{51}$ and $R^{61}$ are the same as defined above, which is prepared by reacting the ketone compound [IX] with a corresponding phosphoryl halide or a corresponding sulfonic acid compound, etc., in the presence or absence of a basic compound (e.g. a tri-lower alkylamine, a 4-di-lower alkylaminopyridine, etc.).

The reaction of the desired compound [I] and a reactive derivative of the ketone compound [IX] is carried out in the presence or absence of a base.

The base may be any conventional base, but preferably a tri-lower alkylamine, a 4-di-lower alkylaminopyridine, etc.

The reaction is preferably carried out in an appropriate solvent or without a solvent under cooling, for example, at a temperature from −5° C. to 0° C., and the solvent may be any conventional inert solvent such as anhydrous acetonitrile, tetrahydrofuran, methylene chloride, etc.

The "lower alkyl group" of the present invention means alkyl groups having 1 to 6 carbon atoms, preferably having 1 to 4 carbon atoms, and the "lower alkanoyl group" means alkanoyl groups having 2 to 6 carbon atoms, preferably having 2 to 4 carbon atoms.

The present invention is illustrated in more detail by the following Example and Reference Example, but should not be construed to be limited thereto.

EXAMPLE 1

(1) To a mixture of (3S)-3-amino-3-carboxypropionic acid methyl ester hydrochloride (155 g), sulfuric acid (433 g), potassium bromide (402 g) and water (1900 ml) is added dropwise a solution of sodium nitrite (69.8 g) in water (150 ml) at a temperature from 10° C. to 12° C. over a period of 45 minutes. After the addition, the mixture is stirred at a temperature from 10° C. to 15° C. for two hours. The reaction solution is extracted with ethyl acetate, and the extract is washed, dried, and concentrated under reduced pressure at a temperature below 35° C. to give (3S)-3-bromo-3-carboxypropionic acid methyl ester (181.5 g) as an oily product.

$[\alpha]_D^{25}$: −52.60° (c=1.019, methanol)

Optical yield: 100% e.e.

(2) To a solution of the above product (79.4 g) in ethanol (500 ml) is added phenylmethanethiol potassium salt (122 g) at 5° C., and the mixture is stirred at room temperature for three hours. The pH value of the reaction solution is adjusted to pH 3–4 with 2N hydrochloric acid, and the mixture is evaporated to remove ethanol, and the mixture is extracted with chloroform. The extract is dried, concentrated under reduced pressure, and thereto is added n-hexane. The precipitated crystals are collected by filtration to give (3R)-3-benzylthio-3-carboxypropionic acid methyl ester (73.9 g).

M.p. 91°–92° C.

$[\alpha]_D^{25}$: +200.78° (c=1.028, methanol)

Optical yield: 98.0% e.e.

(3) To a suspension of sodium borohydride (1.78 g) in tetrahydrofuran (70 ml) is added dimethylsulfide (2.8 ml) at room temperature, and thereto is added dropwise a solution of boron trifluoride-ether complex (6.3 ml) in tetrahydrofuran (10 ml) at room temperature, and the mixture is stirred for 30 minutes. To the mixture is added (3R)-3-benzylthio-3-carboxypropionic acid methyl ester (10 g) at room temperature, and the mixture is stirred for 1.5 hour. After the reaction is completed, to the reaction solution are added successively 2N aqueous sodium hydroxide solution (16 ml), 30% aqueous hydrogen peroxide solution (11 ml), and then further added a saturated aqueous sodium chloride solution. The mixture is extracted with chloroform, and the extract is dried, concentrated under reduced pressure, and the residue is purified by silica gel column chromatography (solvent; n-hexane:ethyl acetate=2:1) to give (3R)-3-benzylthio-4-hydroxybutyric acid methyl ester (7.75 g) as an oily product.

IR (film; cm$^{-1}$): 3458, 1738

$[\alpha]_D^{25}$: +8.30° (c=0.976, methanol)

Optical yield: 99% e.e.

(4) To a solution of the above product (6 g) in chloroform (50 ml) is added pyridine (2.02 ml) at a temperature from 5° C. to 10° C., and thereto is added dropwise thionyl chloride (1.91 ml). The mixture is stirred at the same temperature for one hour. The reaction solution is concentrated under reduced pressure, and thereto is added ethyl acetate. The mixture is washed, dried, and concentrated under reduced pressure. The residue is purified by silica gel column chromatography (solvent; n-hexane:ethyl acetate=10:1) to give (3R)-3-benzylthio-4-chlorobutyric acid methyl ester (4.94 g) as an oily product.

$[\alpha]_D^{25}$: −19.69° (c=0.965, methanol)

Optical yield: 100% e.e.

(5) To the above product (200 mg) is added an ammonia-methanol solution (21.5% w/w) (1.2 ml) at room temperature, and the mixture is stirred for three days. The reaction solution is concentrated under reduced pressure, and to the resulting residue is added water, and the mixture is extracted with methylene chloride. The extract is dried, concentrated under reduced pressure, and the residue is purified by silica gel column chromatography (solvent; chloroform:ethanol=30:1) to give (4R)-4-benzylthio-2-pyrrolidone (135 mg).

M.p. 75°–76° C.

$[\alpha]_D^{25}$: −9.2° (c=1.0, methanol)

Optical yield: 97% e.e.

(6) To a solution of the above product (20 g) in methylene chloride (64 ml) is added phosphorus pentasulfide (4.88 g) at room temperature, and the mixture is stirred at room temperature for five hours. The reaction solution is poured into a saturated sodium hydrogen carbonate solution, and the aqueous layer is extracted with methylene chloride. The extract is dried, concentrated under reduced pressure, and the residue is recrystallized from toluene to give (4R)-4-benzylthiopyrrolidine-2-thione (17.65 g).

M.p. 86°–88° C.

$[\alpha]_D^{25}$: −13.7° (C=1.0, methanol)

Optical yield: 100% e.e.

(7) To the above product (1 g) is added liquid ammonia (20 ml), and the mixture is warmed to a refluxing temperature of ammonia. To the mixture is added sodium (335 mg) over a period of 20 minutes, and the mixture is stirred for 20 minutes. The reaction is quenched by adding thereto aqueous ammonium chloride solution. The mixture is evaporated to remove ammonia, and the pH value of the mixture is adjusted to pH 1–2 with 2N hydrochloric acid. The mixture is extracted with chloroform, and the extract is dried, concentrated under reduced pressure, and thereto is added n-hexane. The precipitated crystals are collected by filtration to give (4R)-4-mercaptopyrrolidine-2-thione (507 mg).

M.p. 73°–75° C.

$[\alpha]_D^{26}$: +109.56° (c=1.067, methanol)

REFERENCE EXAMPLE 1

(1) To a mixture of (3S)-3-amino-3-carboxypropionic acid methyl ester hydrochloride (206 g), sulfuric acid (552 g), potassium bromide (536 g) and water (2510 ml) is added dropwise a solution of sodium nitrite (93 g) in water (200 ml) at a temperature from 10° C. to 12° C. over a period of 45 minutes. The mixture is stirred at the same temperature for 20 minutes, and thereto is added urea (40 g) in portions. The mixture is extracted with ether, and the extract is washed, dried, and concentrated under reduced pressure to give (3S)-3-bromo-3-carboxypropionic acid methyl ester (148 g) as an oily product.

NMR (CDCl$_3$) δ ppm: 2.93–3.10 (1H, m), 3.20–3.40 (1H, m), 3.74 (3H, s), 4.55–4.65 (1H, m), 6.80–7.60 (1H, br)

(2) To a solution of the above product (146 g) in methylene chloride (1.3 liter) is added dimethylformamide (0.76 ml), and thereto is added dropwise oxalyl chloride (106 g) at a temperature from 10° C. to 15° C. over a period of 20 minutes. The mixture is stirred at 25° C. for three hours, and thereto is added dropwise a solution of ammonia in chloroform (2.77% w/w) (1276 g) at a temperature below −30° C. over a period of 30 minutes. After the reaction is completed, activated carbon (14.6 g) is added to the reaction mixture, and the mixture is warmed to 20° C., and filtered. The filtrate is concentrated under reduced pressure, and to the residue is added ethyl acetate. The precipitated crystals is collected by filtration to give (3S)-3-bromo-3-carbamoylpropionic acid methyl ester (99 g).

M.p. 82°–84° C.

$[\alpha]_D^{25}$: −50.6° (c=1.0, methanol)

(3) To a solution of the above product (97 g) in ethyl acetate (1360 ml) is added phenylmethanethiol potassium salt (71 g) at −50° C., and the mixture is stirred at the same temperature for 50 minutes. The mixture is warmed to −30° C. over a period of 20 minutes, and thereto is added water. The precipitated crystals are collected by filtration, washed, and dried by air to give (3R)-3-benzylthio-3-carbamoylpropionic acid methyl ester (76 g).

M.p. 146°–149° C.

$[\alpha]_D^{25}$: +80.3° (c=1.0, methanol)

Optical yield: 100% e.e.

(4) To a solution of the above product (76 g) in dimethylformamide (300 ml) is added dropwise phosphorus oxychloride (69 g) at a temperature from 15° C. to 20° C. over a period of 20 minutes, and the mixture is stirred at the same temperature for one hour. After the reaction is completed, the reaction solution is gradually poured into a mixture of sodium hydrogen carbonate (226 g), ice (100 g), water (1 liter) and ether (1 liter). The ether layer is washed, dried, and concentrated under reduced pressure to give (3R)-3-benzylthio-3-cyanopropionic acid methyl ester (71 g) as an oily product.

NMR (CDCl$_3$)δ ppm: 2.60–2.75 (1H, m), 2.80–2.94 (1H, m), 3.72 (3H, s), 3.70–3.80 (1H, m), 3.90–4.08 (2H, m), 7.25–7.42 (5H, m)

(5) The above product (2.35 g) and cobalt chloride·hexahydrate (2.38 g) are dissolved in methanol (44 ml), and thereto is added sodium borohydride (647 mg) at a temperature from −35° C. to −25° C. over a period of 30 minutes. After the addition, the mixture is warmed to −10° C. over a period of 30 minutes. After the reaction is completed, to the mixture is added 15% hydrogen chloride-methanol solution (10 ml), and the mixture is stirred at 20° C. for 30 minutes. The reaction solution is filtered through celite, and the filtrate is concentrated under reduced pressure, and the residue is dissolved in methanol (30 ml). To the mixture is added 15% ammonia-methanol solution (2.5 ml) at 10° C., and the mixture is concentrated under reduced pressure. To the residue is added chloroform (50 ml), and the mixture is filtered through celite. The filtrate is concentrated under reduced pressure, and the residue is purified by silica gel column chromatography (solvent; chloroform→chloroform:ethanol=20:1) to give (3R)-3-benzylthio-3-aminomethylpropionic acid methyl ester (2.3 g).

The above product is dissolved in dimethylformamide (10 ml), and the mixture is refluxed for two hours. After the reaction is completed, the mixture is evaporated to remove the solvent. The residue is dissolved in chloroform (100 ml), and the mixture is washed, dried and concentrated under reduced pressure. The residue is purified by silica gel column chromatography (solvent; n-hexane:ethyl acetate= 1:1→1:2) to give (4R)-4-benzylthio-2-pyrrolidone (820 mg).

M.p. 75°–76° C.

$[\alpha]_D^{25}$: −9.2° (c=1.0, methanol)

Optical yield: 100% e.e.

(6) The above product (761 mg) is suspended in toluene (22 ml), and thereto is added a Lawson reagent [2,4-bis(4-methoxyphenyl)-1,3-dithia-2,4-diphosphetane-2,4-disulfide] (743 mg), and the mixture is refluxed for 10 minutes. After the reaction is completed, the mixture is evaporated to remove the solvent, and the residue is purified by silica gel column chromatography (solvent; n-hexane:ethyl acetate=4:1) to give (4R)-4-benzylthiopyrrolidine-2-thione (750 mg).

M.p. 86°–88° C.

$[\alpha]_D^{25}$: −13.7° (c=1.0, methanol)

Optical yield: 100% e.e.

(7) The above product (500 mg) is added liquid ammonia (10 ml), and thereto is added sodium (140 mg) over a period of 15 minutes while liquid ammonia is refluxed. The mixture is stirred at the same temperature for 15 minutes. After the reaction is completed, to the mixture is added ammonium chloride (206 mg), and the mixture is evaporated to remove liquid ammonia. To the residue are added ion exchange resin (Diaion SK-1B (H$^+$)) (16 ml) and water (10 ml), and the mixture is stirred and then filtered. The filtrate is evaporated to remove water, and to the residue is added chloroform. The mixture is dried, evaporated to remove the solvent, and the residue is purified by silica gel column chromatography (solvent; n-hexane:ethyl acetate=9:1) to give (4R)-4-mercaptopyrrolidine-2-thione (171 mg).

M.p. 73°–75° C.

$[\alpha]_D^{26}$: +109.3° (c=1.0, methanol)

Optical yield: 100% e.e.

EFFECTS OF THE INVENTION

According to the present invention, 4-mercaptopyrrolidine compounds [I] are easily and industrially advantageously obtained by reacting a novel halogenobutyric acid compound [VI] such as a 3-phenyl-lower alkylthio-4-halogenobutyric acid lower alkyl ester, etc. and the amine compound [VII].

Particularly, in the preparation of the compound [I] wherein R is a hydrogen atom, ammonia per se can be used as an amine compound [VII] in the present invention instead of a precursor of ammonia such as phthalimide, sodium diformylamide, etc.

Besides, all the reactions of the process of the present invention can proceed without racemization so that optically active desired compound [I] and the optically active compound [VIII] can selectively be obtained from the optically active starting compounds.

Especially, as shown in the following reaction scheme, since the reaction of the compound [II] and the compound [III] proceeds with 100% stereo-inversion, the desired compound [I] having 4R-configuration, which is more useful as an intermediate for preparing carbapenem antibacterial agents, can selectively be obtained from L-aspartic acid which is easily obtained at low cost.

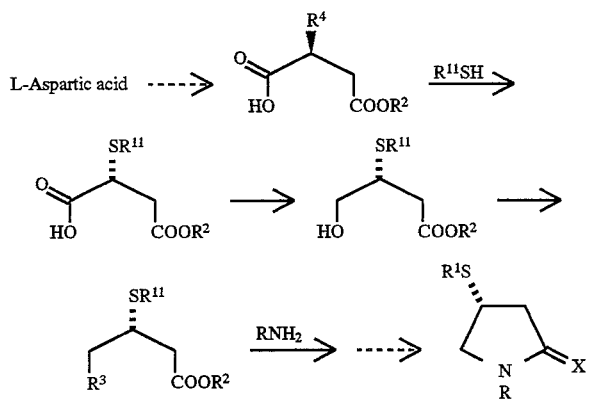

Thus, the method of the present invention can give (4R)-4-benzylthio-2-pyrrolidone in 41% yield while the method disclosed in Japanese Patent First Publication (Kokai) No. 279328/1993 gives it from (3S)-3-bromo-3-carboxypropionic acid methyl ester merely in 18% yield.

Accordingly, the desired compound [I] can be obtained at low cost by the process of the present invention, which is industrially most advantageous.

What is claimed is:

1. A process for preparing a 4-mercaptopyrrolidine compound of the formula [1]:

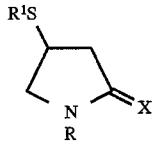 [I]

wherein R is a hydrogen atom, a lower alkyl group or a lower alkanoyl group, $R^1$ is a hydrogen atom or a protecting group for thiol group, and X is an oxygen atom or a sulfur atom, which comprises reacting a halogenobutyric acid compound of the formula [VI]:

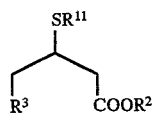 [VI]

wherein $R^{11}$ is a protecting group for thiol group, $R^2$ is a hydrogen atom or a protecting group for carboxyl group, and $R^3$ is a halogen atom, or a salt thereof, with an amine compound of the formula [VII]:

$RNH_2$ [VII]

wherein R is the same as defined above, or a salt thereof to obtain a compound of the formula:

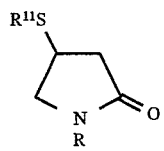

wherein $R^{11}$ and R are the same as defined above, and if necessary, followed by thiocarbonylating the product and/or removing the protecting group for thiol group from the product.

2. The process according to claim 1, wherein R is a hydrogen atom.

3. The process according to claim 1, wherein $R^{11}$ is a phenyl-lower alkyl group and $R_2$ is a lower alkyl group.

4. A halogenobutyric acid compound of the formula [VI]:

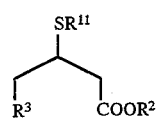 [VI]

wherein $R^{11}$ is a protecting group for thiol group, $R^2$ is a hydrogen atom or a protecting group for carboxyl group, and $R^3$ is a halogen atom, or a salt thereof.

5. The compound according to claim 4, wherein $R^{11}$ is a phenyl-lower alkyl group and $R^2$ is a lower alkyl group.

6. A process for preparing a 4-mercaptopyrrolidine compound of the formula [1]:

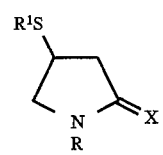 [I]

wherein R is a hydrogen atom, a lower alkyl group or a lower alkanoyl group, $R^1$ is a hydrogen atom or a protecting group for thiol group, and X is an oxygen atom or a sulfur atom, which comprises (i) reacting a halogenosuccinic acid compound of the formula [III]:

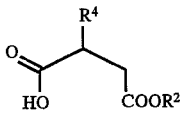 [II]

wherein $R^2$ is a hydrogen atom or a protecting group for carboxyl group, and $R^4$ is a halogen atom, or a salt thereof, with a thiol compound of the formula [III]:

$R^{11}SH$ [III]

wherein $R^{11}$ is a protecting group for thiol group, or a salt thereof, to give a mercaptosuccinic acid compound of the formula [IV]:

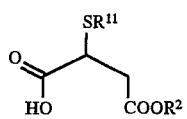

wherein R¹¹ and R² are the same as defined above, (ii) subjecting the compound [IV] or a salt thereof to reduction to give a hydroxybutyric acid compound of the formula [V]:

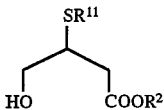

wherein R¹¹ and R² are the same as defined above, (iii) halogenating the compound [V] or a salt thereof to give a halogenobutyric acid compound of the formula [VI]:

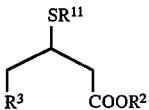

wherein R³ is a halogen atom, and R¹¹ and R² are the same as defined above, (iv) reacting the compound [VI] or a salt thereof with an amine compound of the formula [VII]:

RNH₂      [VII]

wherein R is the same as defined above, or a salt thereof, to obtain a compound of the formula:

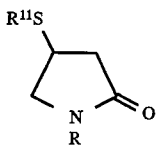

wherein R¹¹ and R are the same as defined above, and if necessary, (v) followed by thiocarbonylating the product and/or removing the protecting group for the thiol group from the product.

7. A process for preparing a 2-(pyrrolidin-4-ylthio)-6-(1-hydroxyethyl)-1-methylcarbapen-2-em-3-carboxylic acid derivative of the formula [VIII]:

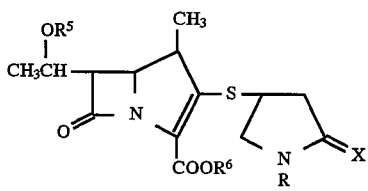

wherein R⁵ is a hydrogen atom or a protecting group for hydroxy group, R⁶ is a hydrogen atom or an ester residue, R is a hydrogen atom, a lower alkyl group or a lower alkanoyl group and X is an oxygen atom or a sulfur atom, or a salt thereof, which comprises reacting a halogenobutyric acid compound of the formula [VI]:

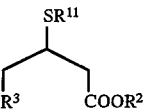

wherein R¹¹ is a protecting group for thiol group, R² is a hydrogen atom or a protecting group for carboxyl group, and R³ is a halogen atom, or a salt thereof, with an amine compound of the formula [VII]:

RNH₂      [VII]

wherein R is the same as defined above, or a salt thereof, to obtain a compound of the formula

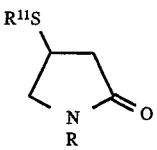

wherein R¹¹ and R are the same as defined above, and if necessary, thiocarbonylating the product and/or removing the protecting group for thiol group from the product, to give a 4-mercaptopyrrolidine compound of the formula [I]:

[I]

wherein R¹ is a hydrogen atom or a protecting group for thiol group, R and X are the same as defined above, followed by converting the compound [I] by a conventional method into the 1-methylcarbapenem derivative of the formula [VIII].

8. The process according to claim 2, wherein R¹¹ is a phenyl-lower alkyl group and R² is a lower alkyl group.

* * * * *